(12) United States Patent
Nippoldt et al.

(10) Patent No.: US 8,095,225 B2
(45) Date of Patent: *Jan. 10, 2012

(54) ROBUST HIGH POWER AND LOW POWER CARDIAC LEADS HAVING INTEGRATED SENSORS

(75) Inventors: Douglas D. Nippoldt, Centerville, MN (US); Thomas D. Brostrom, Wayzata, MN (US); Richard J. O'Brien, Hugo, MN (US); Michael A. Schugt, Saint Paul, MN (US); Scott J. Davis, Maple Grove, MN (US); Yaling Fan, Savage, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

This patent is subject to a terminal disclaimer.

(21) Appl. No.: 12/411,082

(22) Filed: Mar. 25, 2009

(65) Prior Publication Data

US 2009/0248108 A1 Oct. 1, 2009

Related U.S. Application Data

(60) Provisional application No. 61/207,854, filed on Mar. 25, 2008.

(51) Int. Cl.
*A61N 1/05* (2006.01)
(52) U.S. Cl. ............ 607/122; 600/488; 600/486
(58) Field of Classification Search .......... 607/122; 600/488
See application file for complete search history.

(56) References Cited

U.S. PATENT DOCUMENTS

| | | | | |
|---|---|---|---|---|
| 4,274,423 A | * | 6/1981 | Mizuno et al. | 600/488 |
| 5,222,506 A | | 6/1993 | Patrick et al. | |
| 5,324,326 A | * | 6/1994 | Lubin | 607/122 |
| 5,564,434 A | * | 10/1996 | Halperin et al. | 600/488 |
| 5,899,927 A | | 5/1999 | Ecker et al. | |
| 6,171,252 B1 | * | 1/2001 | Roberts | 600/485 |
| 6,183,305 B1 | | 2/2001 | Doan et al. | |
| 7,087,017 B2 | | 8/2006 | Christopherson et al. | |
| 7,254,450 B2 | | 8/2007 | Christopherson et al. | |
| 7,286,884 B2 | | 10/2007 | Marshall et al. | |
| 2006/0264925 A1 | | 11/2006 | Sharareh et al. | |
| 2009/0248107 A1 | * | 10/2009 | Nippoldt et al. | 607/36 |

FOREIGN PATENT DOCUMENTS

| | | |
|---|---|---|
| EP | 0314937 | 10/1989 |
| WO | 0025862 | 5/2000 |
| WO | W02005058133 | 6/2005 |
| WO | W02005072817 | 8/2005 |
| WO | W02005107583 | 11/2005 |
| WO | W02006069323 | 6/2006 |
| WO | W02007120884 | 10/2007 |

OTHER PUBLICATIONS

International Search Report, PCT/US2009/038260, 3 pages.
International Search Report, PCT/US2009/038242, 3 pages.

* cited by examiner

*Primary Examiner* — Kennedy Schaetzle
(74) *Attorney, Agent, or Firm* — Michael C. Soldner (57) ABSTRACT

A lead of an implantable medical device system having an elongated lead body, a sensor coupled to the lead body and extending from a proximal end to a distal end, and a distal lead adaptor having a first arm extending distally from the distal end of the sensor to a first arm end, a second arm extending distally from the distal end of the sensor to a second arm end, and a third arm extending between the first arm end and the second arm end, wherein the first arm, the second arm, and the third arm form an open portion.

14 Claims, 13 Drawing Sheets

ROBUST HIGH POWER AND LOW POWER CARDIAC LEADS HAVING INTEGRATED SENSORS

RELATED APPLICATION

This application claims the benefit of and priority to U.S. Provisional Application Ser. No. 61/207,854, filed Mar. 25, 2008, entitled, "Robust High Power and Low Power Cardiac Leads Having Integrated Sensors," the contents of which are incorporated by reference herein in its entirety.

CROSS-REFERENCE TO RELATED APPLICATIONS

Cross-reference is hereby made to the commonly assigned related U.S. patent application Ser. No. 12/411,058, entitled "ROBUST HIGH POWER AND LOW POWER CARDIAC LEADS HAVING INTEGRATED SENSORS", to Nippoldt et al. and U.S. patent application Ser. No. 12/411,033, entitled "ROBUST HIGH POWER AND LOW POWER CARDIAC LEADS HAVING INTEGRATED SENSORS", to Nippoldt et al., both incorporated herein by reference in their entireties.

FIELD

The present disclosure relates to medical electrical leads having one or more sensors coupled to a portion thereof which are cooperatively designed with desired mechanical properties to reduce strain on and signal artifacts from said one or more sensors.

BACKGROUND

Implantable cardiac leads having sensors in addition to exposed coil, tip, and/or ring electrodes used to deliver electrical stimulation to myocardial tissue and/or to sense electrical cardiac activity as well as monitor one or more physiologic parameters. Such leads include elongated electrical conductors and are fabricated of a biocompatible polymeric material, for example, polyurethane or silicone. Sensors have previously been coupled to cardiac leads. Since the leads are coupled to the myocardium they must possess flexibility and strength. If the sensor or sensors is disposed near the distal end of the lead the forces from the contractions can directly impinge on the sensor surface possibly causing damage and signal artifacts. If one or more electrodes are disposed distal to a sensor, one or more electrical conductors must pass by or through the sensor thereby increasing the complexity of the sensor assembly and possibly changing the dimension of the sensor package. The resulting package can thus have differing strain sensitivity that adds signal artifacts and reduces long term stability of the sensor disposed therein. A need thus exists for a cooperatively designed sensor packaging and lead body that increases mechanical reliability, operating life and improves long term sensor stability.

DETAILED DESCRIPTION OF THE ILLUSTRATED EMBODIMENTS

In the following detailed description, references are made to illustrative embodiments for methods and apparatus including very small sensors coupled to medical electrical leads. This disclosure provides enhanced mechanical resiliency to very small sensors coupled to medical electrical leads that are cooperatively designed and fabricated.

One of the challenges in placing small sensors on a cardiac lead is to make sure that the sensor only responds to the desired physical parameter. The heart is a dynamic environment and cardiac leads flex as the heart beats. The flexing of the cardiac lead transmits forces to a sensor placed on the lead and, if not managed appropriately, will induce a strain-related output signal artifact from the sensor. The disclosure is directed to a cooperative cardiac lead and sensor assembly wherein the sensor package or capsule is mechanically strengthened in at least one specific bending axis. The lead is then designed and constructed so that the lead has a desired bending orientation. This can be accomplished via a variety of different ways. One is to attach or couple different mechanical structures about the longitudinal axis of the lead (e.g., a pair of parallel cables in one portion while coils are used in another). Another is to form one or more lumens within the lead body that cause the lead body to bend in the desired direction (e.g., ovoid-shaped lumen or lumens, V- or U-shaped lumens). Of course a combination of structure and lumen can be used to achieve the desired bending characteristic(s) for the lead. Also, one or more portions of the lead body can be selectively managed with lumens and/or structures; for example, only the distal portion or only the distal and intermediate portion and the like.

The necessary electrical conductors for a given cardiac application may, or may not, provide a preferred bending orientation of the lead body that is compatible with the robust axis of the sensor. According to the invention, lumens, cables or the like can be introduced into the lead body to provide the sensor lead with the optimum preferred bending axis.

In one embodiment a coaxial sensor communication coil (for bi-directional communication) is disposed in a lumen parallel to another similarly-sized cable (e.g., a torque coil used to advance an active fixation coil for insertion into adjacent tissue) so that the lead body is mechanically constrained in one dimension (i.e., laterally across the pair of coils) and not constrained in another (i.e., longitudinally perpendicular to the coils). In another embodiment, the lead body is pre-formed via a heat treatment or annealing treatment on one or more sides so that the stiffened axis of the sensor is aligned with the pre-formed bending direction of the lead body. In lieu of or in addition to pre-forming or pre-bending the lead body the biocompatible material of the lead body can have a differing modulus so that it is essentially softer on one side thereby causing the lead body to flex, or bend, toward the softer side. In another embodiment, the lead body can be formed so that it is not iso-diametric or circular in cross section, that is, the lead body is designed to have a relatively flattened cross-section.

The sensor package is then cooperatively designed so that it has a mechanically robust axis aligned with the not constrained bending direction of the lead body. In the case that a stylet or wire needs to be advanced beyond the sensor package, a receiving bore or partial bore needs to be designed in the package. Accordingly, the package needs to be designed to accommodate the bore and the related structural impact needs to be considered. Thus, one aspect of the foregoing involves aligning the package so that the lead body bends in the direction of maximum stiffness of the package. In one embodiment an internal longitudinal torque coil used for advancing a helical member at the distal tip of the lead promotes fixation of the lead to tissue. Also a coaxial communications bus couples to the sensor and these two relatively major components of the lead body (i.e., the torque coil and the communications bus) define a desired bending direction (in the direction perpendicular to the plane of the two coils).

Another embodiment of the invention includes more than one sensor coupled to the lead body. For example, a pair of pressure sensors coupled so that one sensor is adapted to reside in the right ventricle and one sensor is adapted to reside in the right atrium. In a variation on this embodiment, both of the sensors are designed according to the disclosure to have a mechanically robust axis aligned with the not constrained bending direction of the lead body to impart a desired bending direction associated with the specific sensor, resulting in the lead body having two different preferred bending directions. This aspect of the invention allows each sensor to more likely have its sensing surface facing toward the blood residing in its respective chamber and away from the chamber tissue.

In one embodiment a medical electrical lead is provided that includes an elongated lead body formed of a biocompatible material that has a desired longitudinal bending direction in at least one of a proximal end portion, an intermediate portion and a distal portion. The lead body includes at least one elongated conductor disposed within the lead body that couples to a physiologic sensor coupled to the conductor and is adapted to measure a parameter and provide a signal through said conductor. The sensor is disposed in a biocompatible sensor package that possesses a longitudinal strain-insensitive axis that aligns with the desired physical bending direction of the lead body.

Thus, the disclosure provides methods and structures for deliberately introducing design features in a lead body to create a preferential bending direction to accommodate the most strain-insensitive bending axis of a sensor or sensors coupled to the lead. That is, the lead and sensor system can be cooperatively designed to provide one or more axes of bending and enhanced mechanical strength, respectively. Such a system can be fabricated according to the invention without compromising the performance characteristics of a manually deployable cardiac therapy delivery lead.

Figure 1A:
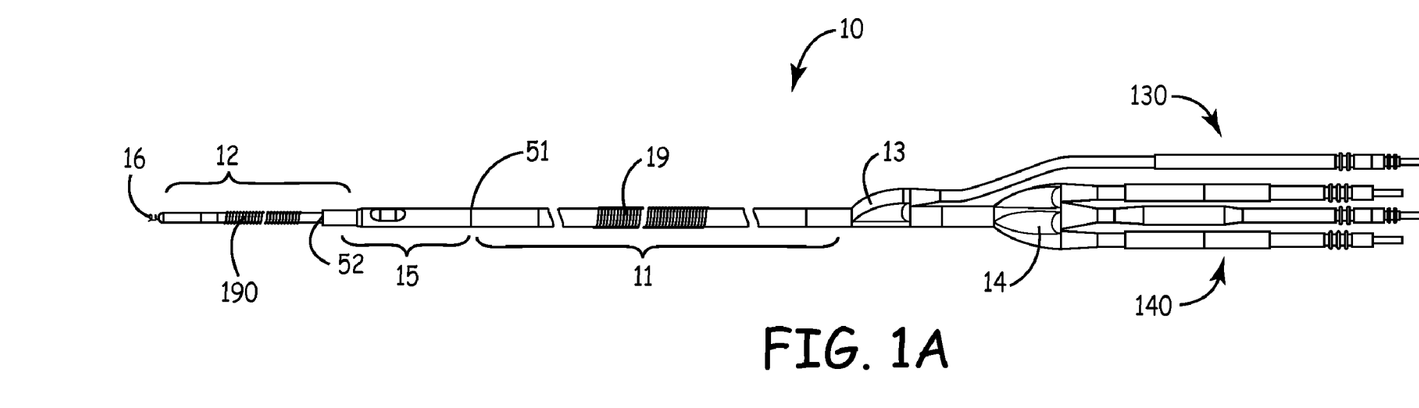
FIGS. 1A-1B are plan views of a medical electrical lead according to embodiments of the disclosure.
Figure 1B:
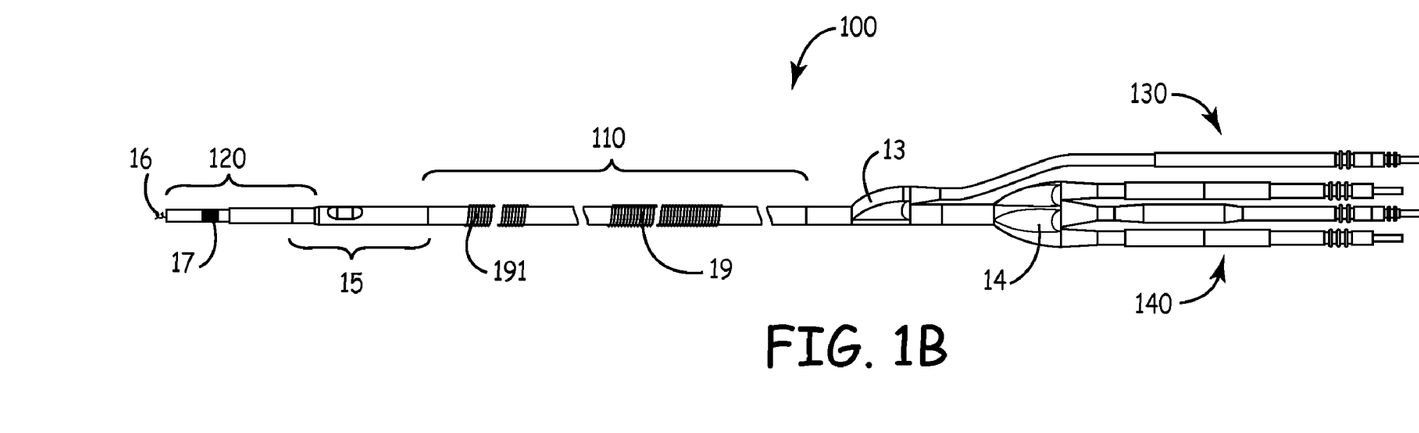

FIGS. 1A-B are plan views of medical electrical leads according to alternate embodiments of the present invention. FIG. 1A illustrates lead 10 including a lead body first portion 11, a lead body second portion 12 and a sensor assembly 15 coupled in between first portion 11 and second portion 12; first portion 11 includes a first high voltage defibrillation electrode 19 and second portion 12 includes a second high voltage defibrillation electrode 190 and a low voltage tip electrode 16. FIG. 1B illustrates lead 100 including a lead body first portion 110, a lead body second portion 120 and sensor assembly 15 coupled in between first portion 110 and second portion 120; in this embodiment, first portion 110 includes first high voltage defibrillation electrode 19 and a second high voltage defibrillation electrode 191 while second portion includes a low voltage ring electrode 17 and low voltage tip electrode 16. Any appropriate low voltage and high voltage electrode designs known to those skilled in the art may be incorporated into embodiments of the present invention, therefore the present invention is not limited to the forms of these electrodes illustrated in FIGS. 1A-B. Although FIGS. 1A-B illustrate first portion 11, 110 including at least one electrode, first lead body portions according alternate embodiments of the present invention need not include any electrodes. Furthermore, according to alternate embodiments, a second lead body portion, i.e. portions 12, 120, may include one or more fluid infusion ports positioned for example where tip electrode 16 or ring electrode 17 are positioned.

FIGS. 1A-B further illustrate lead body first portion 11, 110 joined to a sensor connector leg 130, via a first transition sleeve 13, and to electrode connector legs 140, via a second transition sleeve 14; connector legs 130 and 140 are adapted to electrically couple a sensor of sensor assembly 15 and electrodes 16, 17, 19 and 190/191, respectively to an IMD in a manner well known to those skilled in the art.

Figure 1C:
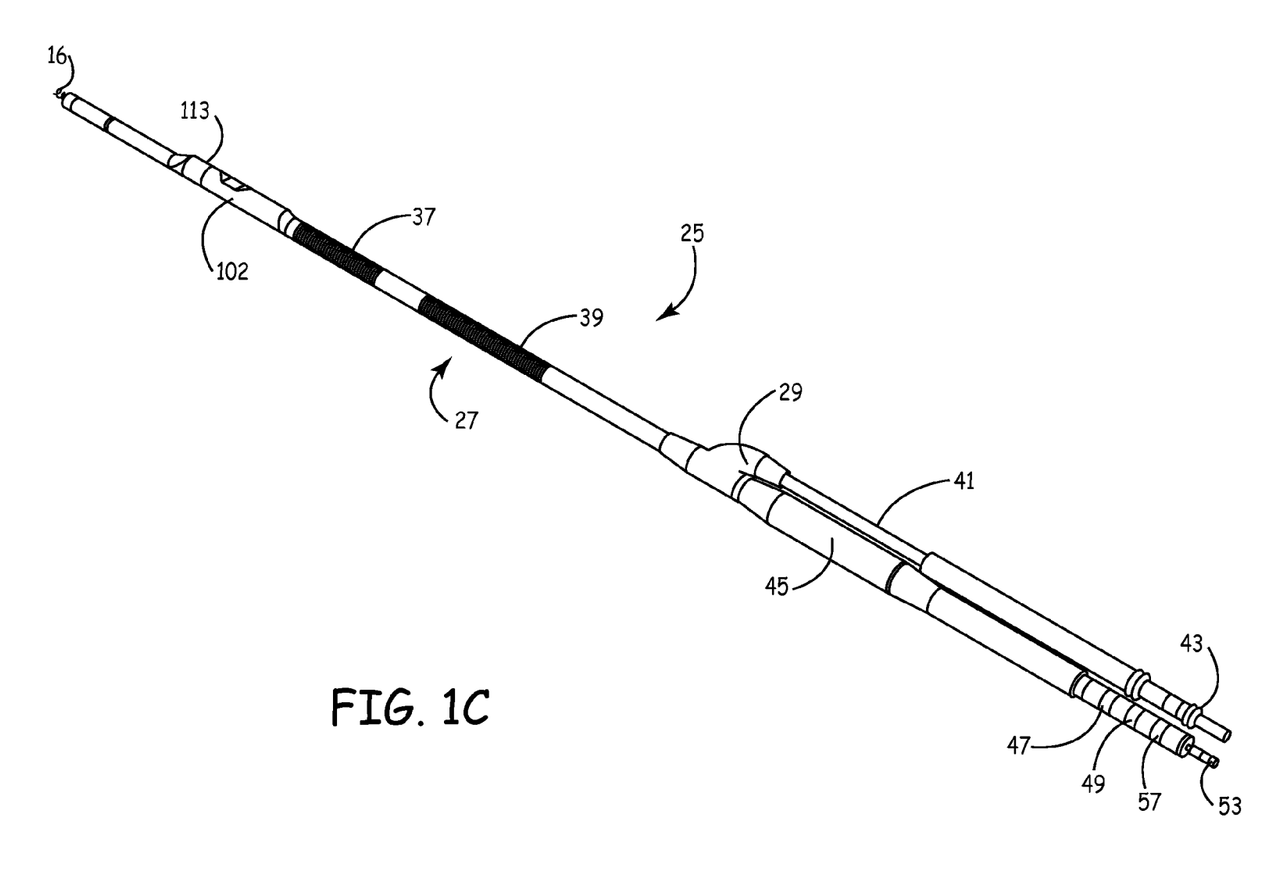
FIG. 1C is a plan view of a medical electrical lead according to an embodiment of the disclosure.

FIG. 1C is a plan view of a medical electrical lead according to an embodiment of the disclosure. As illustrated in FIC. 1C, lead 25 may include a lead body portion 27 extending from a connector 29 to a sensor 102 as described herein. Lead also includes a ring electrode 35 distal to the sensor 102, a right ventricular (RV) electrode 37 and a superior vena cava (SVC) electrode 39 positioned proximal to the sensor 33. Connector 29 of lead 25 includes a connector leg 41 having a connector ring 43 for electrically coupling the sensor 102 to circuitry within an IMD housing, and a second connector leg 45 having a first connector ring 47, a second connector ring 49, a third connector ring 51 and a fourth connector ring 53 for electrically coupling the SVC electrode 39, RV electrode 37, ring electrode 33 a helical tip electrode 16, respectively, to corresponding circuitry within IMD housing via conductors (not shown) extending between the electrodes and the connector rings.

Figure 1D:
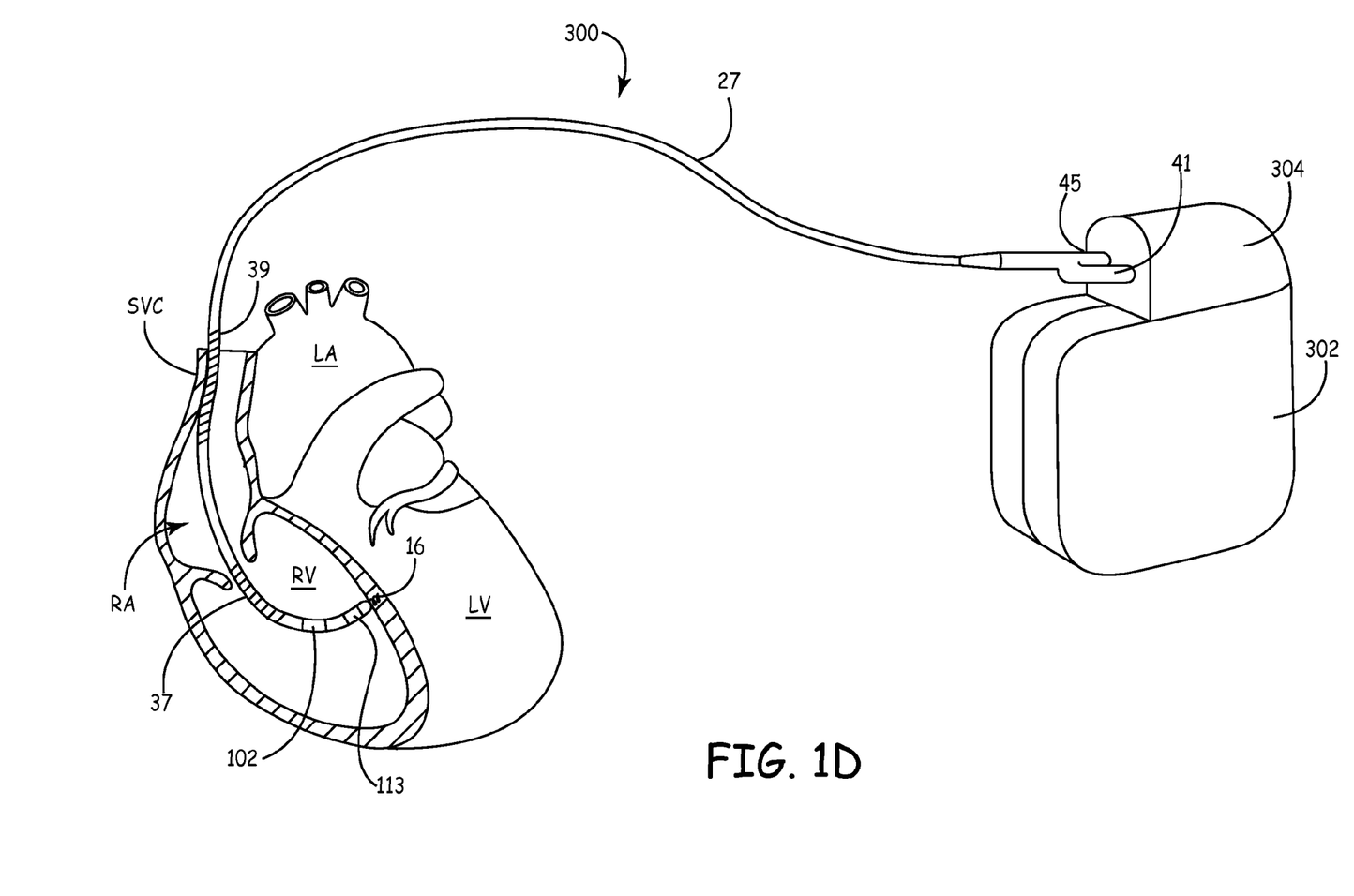
FIG. 1D is a schematic diagram of an implantable medical device system utilizing a pressure sensing lead according to an embodiment of the disclosure.

FIG. 1D is a schematic diagram of an implantable medical device system utilizing a pressure sensing lead according to an embodiment of the disclosure. As illustrated in FIG. 1D, an implantable medical device system 300 that utilizes sensor 102 includes any one of sensor leads described above, such as sensor lead 25, for example, and an implantable medical device housing 302. Housing 302 contains circuitry (not shown) for operating the implantable medical device, as is known in the art, and includes a header 304 for receiving connector rings 43-53 to electrically couple the lead 25, including sensor 102, to the circuitry contained in housing in a known fashion.

Figure 2:
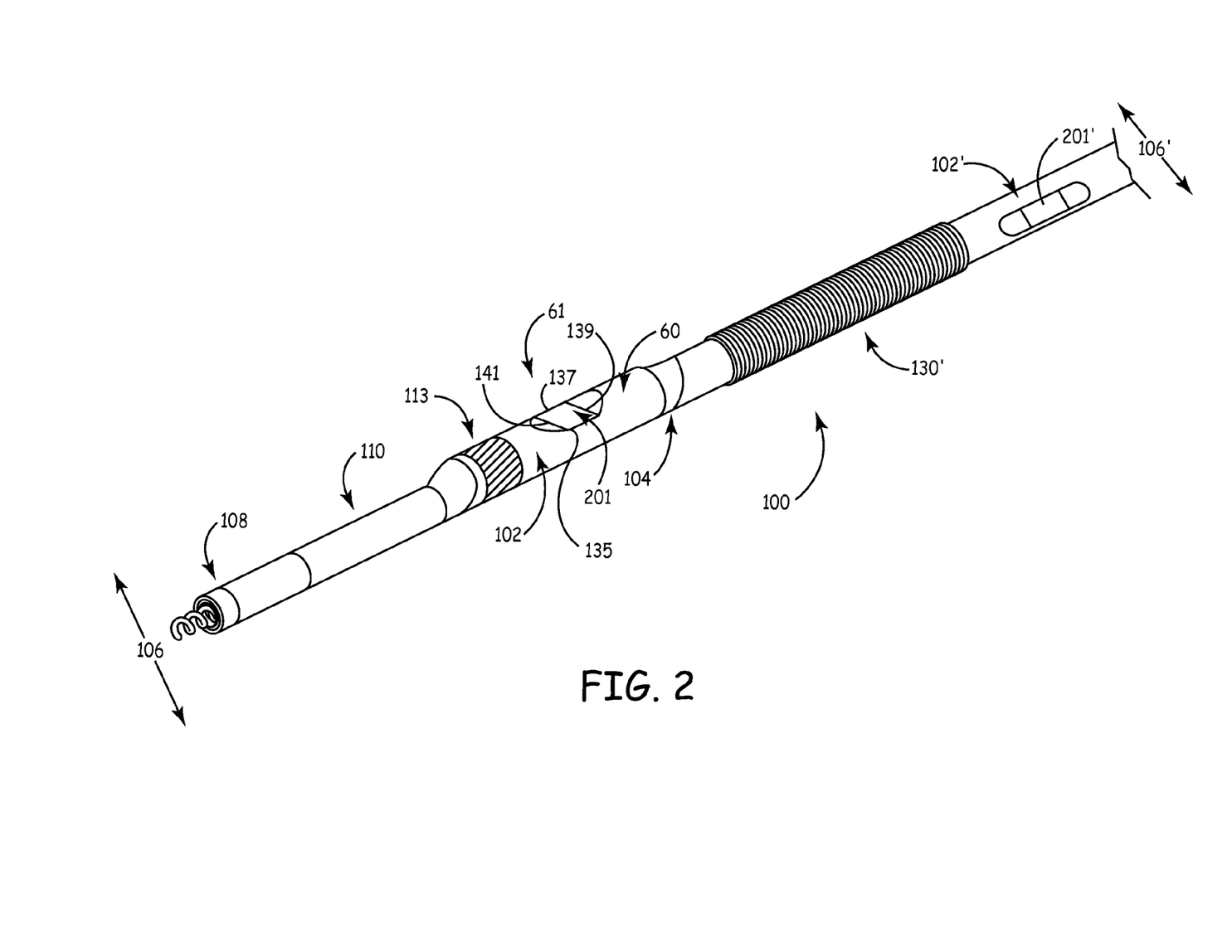
FIG. 2 is a perspective view of a distal portion of a pressure sensing lead according to an embodiment of the disclosure.

FIG. 2 is a perspective view of a distal portion of a pressure sensing lead according to an embodiment of the disclosure. As illustrated in FIG. 2, a sensor 102 according to the embodiments of the disclosure includes a sensor body 60 having sensor membrane 201 positioned within a cutout portion 61 of the sensor body 60. The membrane 201 extends laterally between a first side 135 and a second side 137, and extends longitudinally (perpendicular to the lateral extension) between a first end 139 and a second end 141 distal along the lead body 27 relative to the first end 139.

Undesirable deflection of sensor membrane 201 of pressure sensor 102 may occur as a result of fluctuations in the level of pressure present in a cardiac chamber. In order to best sense such deflections, minimize signal artifacts, and limit stress upon the sensor 102, it is desirable to ensure that the membrane 201 sweeps in the lateral direction extending between the first side 135 and the second side 137 (along the axis defined by arrow 106), rather than in the longitudinal direction extending between the first end 139 and the second end 141 when coupled to myocardial tissue.

Adjacent to the sensor 102 is optional pacing and sensing ring electrode 113. Coupled to the sensor 102 is a relatively flexible member 110 coupling from the ring electrode 113 to optional extendable and retractable helix sub-assembly 108 used to fixate the tip of lead 100 to adjacent myocardial tissue. A proximal sensor lead portion 104 includes optional right ventricular (RV) coil electrode 130' used for high energy defibrillation therapy delivery. Proximal to the RV coil electrode 130' is an optional second pressure sensor 102' having a sensing membrane 201'. Lead 100 may include an optional superior vena cava (SVC) coil electrode can be coupled to the lead 100 proximal to the second pressure sensor 102'.

Although not depicted in FIG. 2, within the lead body 27 in the proximal sensor lead portion 104 a set of electrical conductors reside within a multi-lumen structure. For example, if the sensor lead 100 is designed only for sensing, two coils will extend at least to the sensor 102. The first, a torque coil 129, resides in a lumen and is used during implantation (to enhance the so-called "pushability" of the lead 100). The second, a co-axial communication bus coil 127 (see FIG. 4) resides in a different lumen for carrying signals to and from the circuitry of sensor 102. As noted above, the two coils can be used to establish a desired bending direction for the body of the lead 100 and the sensor 102 (i.e., in a lateral direction extending between the first side 135 and the second side 137 of the sensor membrane 201). This desired bending direction results from the slight compressive load placed upon the lead 100 shortly after implantation.

In other configurations, for example if the sensor lead 100 is designed for sensing pressure and cardiac activity and/or pacing a heart, then the torque coil used during implant can be electrically coupled to the tip electrode (e.g., helix of helical sub-assembly 108) and optionally another elongated cable-type conductor can be routed to the ring electrode 113. In this configuration, the desired bending direction remains the same due to the two coils orientation relative to the sensor membrane 201.

Also depicted in FIG. 2 is an optional second sensor 102' having a sensor membrane 201' which can have an arbitrary orientation relative to sensor member 201, applying the principles described and depicted herein. That is, in the event that the second sensor 102' is intended to sense pressure within the right atrium (RA), the relative orientation of the two sensors 102,102' can be different or changed during fabrication of the lead 100 to promote a different lateral motion for the sensor 102' (as depicted by arrow 106'). If the second sensor 102' is adapted to sense RA pressures, then in addition to having lateral motion of the membrane 201' relative to the lead 100, the membrane 201' should face away from the nearest wall of the RA. Also, the second sensor 102' can utilize the same digital sensor protocol carried upon the sensor communication bus as the first sensor 102.

Figure 3:
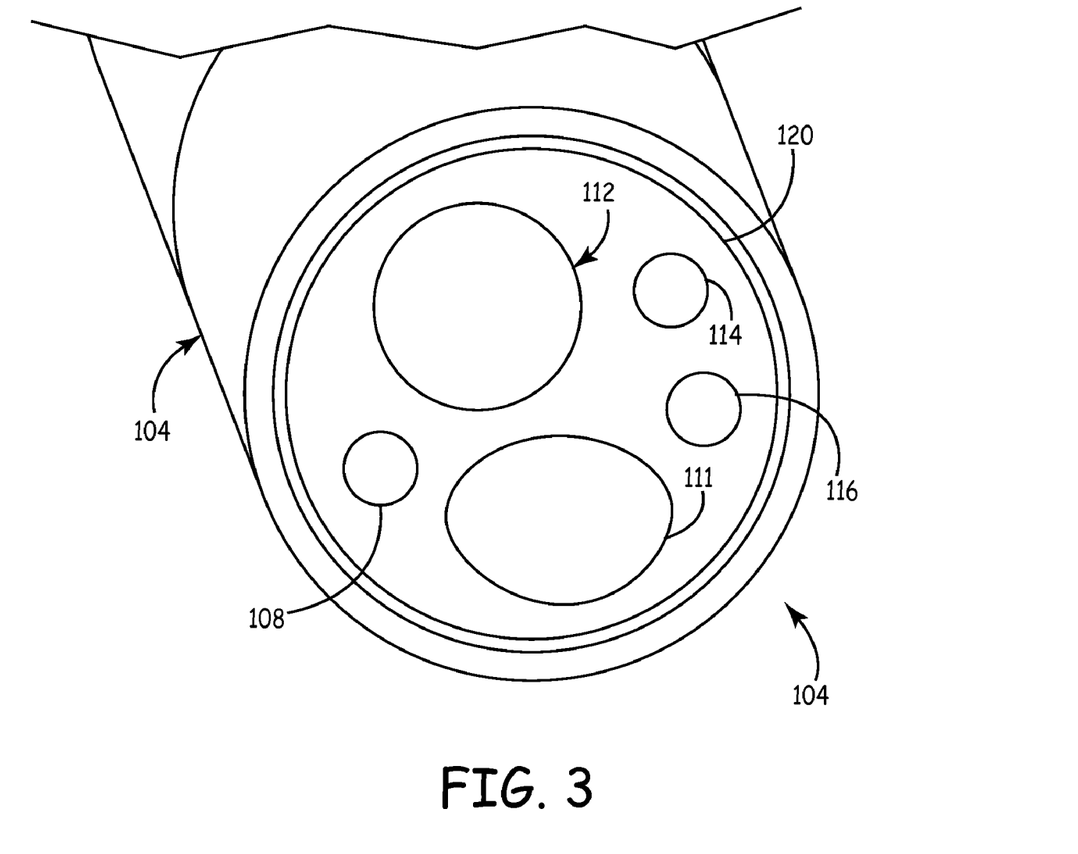
FIG. 3 is a cross-sectional view of a portion of a lead body wherein two major elongated lumens, a sensor lumen and a torque coil lumen are spaced apart and disposed whereby they define a plane which promotes a bending direction perpendicular to the defined plane.

FIG. 3 is a cross-sectional view of a portion of a lead body 104 wherein two major elongated lumens 111,112 (denoted as a sensor bus lumen and a torque coil lumen) are spaced apart and disposed whereby they define a plane through the center axis of each, which promotes the desired bending direction, i.e., in a direction extending laterally between the first side 135 and the second side 137 of the membrane 201, perpendicular to the longitudinal direction extending between the first end 139 and the second end 141 of the membrane 201.

As depicted, the lead body portion 27 may also have one or more additional smaller-diameter lumens 108,114,116 configured to receive an SVC cable, an RV cable, and a ring electrode cable lumen, respectively. The lead body 104 is sheathed in an overlay tubing 120 and the penta-lumen is nominally fabricated of Silicone (e.g., MED-4755 made by Nusil Technology of Carpinteria, Calif.). As depicted, the major lumens 111,112 are designed to promote the desired bending direction (indicated generally by arrow 106 of FIG. 3).

Figure 4:
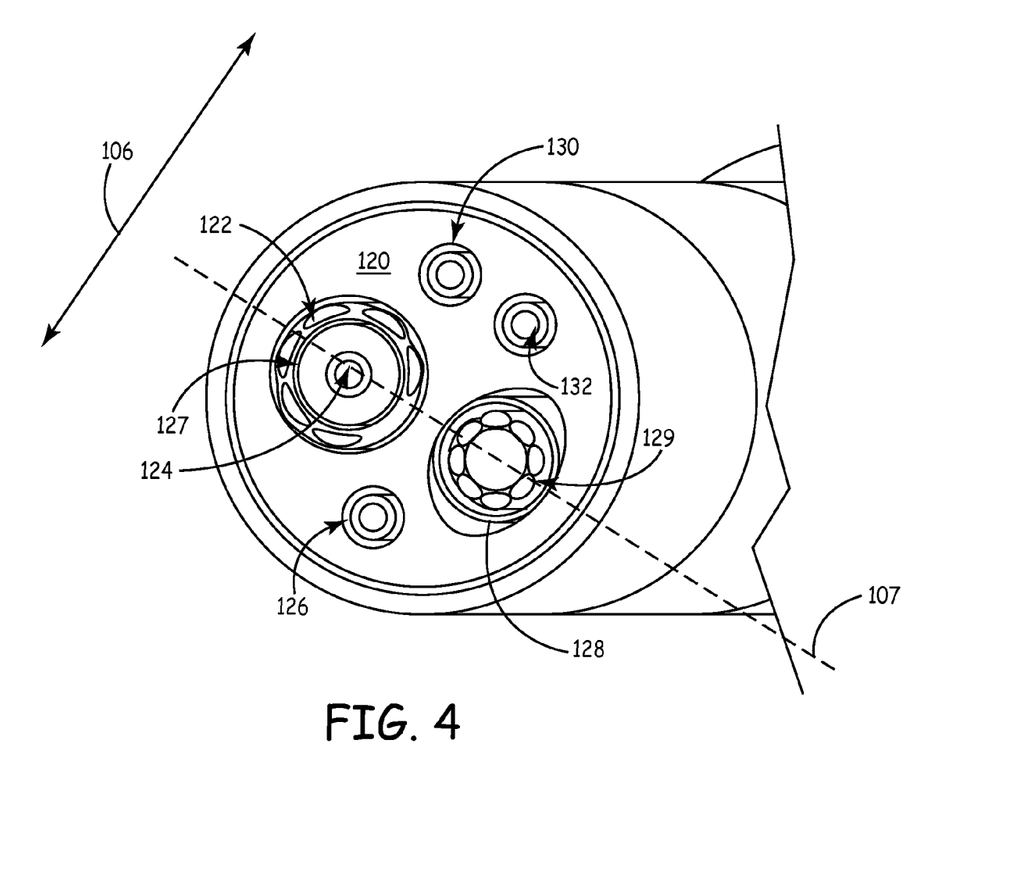
FIG. 4 is a cross-sectional view of the lumens depicted in FIG. 3 and the accompanying components disposed therein; namely, a sensor communication bus coil, a torque coil as well as two high energy cables (SVC cable and RV coil) and a low energy pacing cable (ring cable).

FIG. 4 is a cross-sectional view of the lumens depicted in FIG. 3 and the accompanying components disposed therein; namely, a sensor communication bus coil 127 having an inner sensor bus cable 124 and an outer sensor bus coil 122, a torque coil 129 having an optional covering 128, as well as two high energy cables (SVC cable 126 and RV cable 130) and a low energy pacing and sensing cable (ring cable) 132. The sensor bus coil 122, the sensor bus cable 124, and the torque coil 129 define a plane through the axial center of each, which promotes the desired bending direction extending laterally between the first side 135 and the second side 137 of the membrane 201, perpendicular to the longitudinal direction extending between the first end 139 and the second end 141 of the membrane 201.

Figures 5A, 5B:
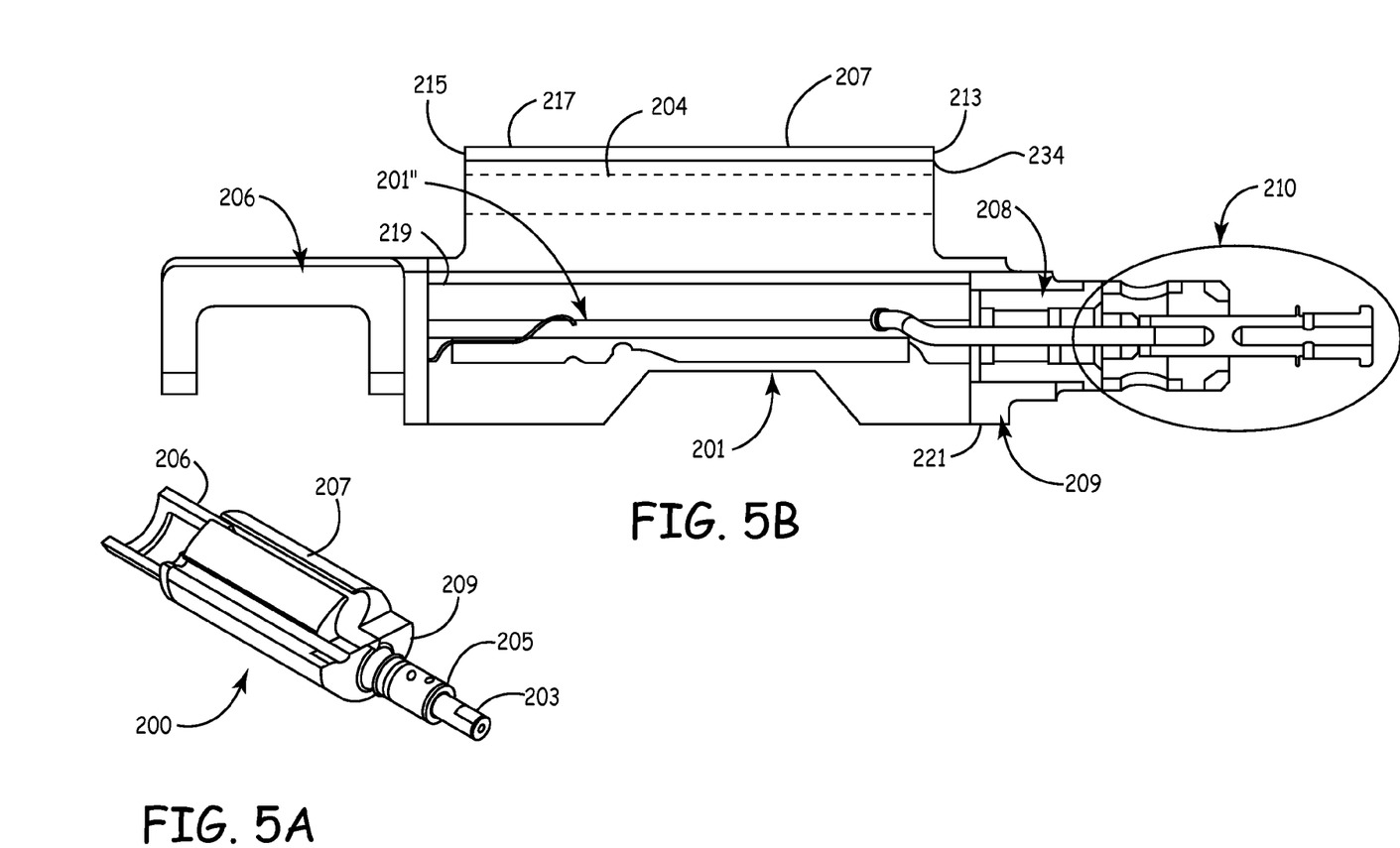
FIG. 5A is a side view of a sensor of a medical electrical lead according to an embodiment of the disclosure.
FIG. 5B is a perspective view of the sensor of FIG. 5A.

FIGS. 5A and 5B depict an embodiment of a sensor package 200 designed and constructed out of titanium according to one form of the disclosure. For example, sensor package 200 may be formed using a suitable titanium alloy, such as Ti 6Al-4V, for example, although other alloys and other materials could suffice. FIG. 5A is a perspective view of the sensor package 200 and FIG. 5B is an elevational side view of the sensor package 200 illustrating an embodiment wherein a relatively thin membrane 201 is used to sense pressure fluctuations on one side of the sensor package 200, and a relatively thicker back housing portion 207 provides an axis of relative stiffness to the sensor package 200 (which is generally perpendicular to the sensor package 200 depicted in FIG. 5B (i.e., perpendicular to the drawing sheet). In practice the axis of stiffness is designed so that it is aligned with providing the desired lateral bending direction of the membrane 201 as that provided by the twin coils described above (and other structures and/or lumens described below in relation to FIGS. 11-14).

As illustrated in FIG. 5A and 5B, back housing portion 207 extends from a top portion 217 to a bottom portion 219, with a proximal end 234 of the top portion 217 extending from a proximal end 213 to a distal end 215. A first bore 204 is formed adjacent to the top portion 217 in back housing portion 207 for receiving the torque coil 129 so that the torque coil 129 extends through the sensor 102 from the proximal end to the distal end of the sensor 102 so as to be parallel to the membrane 201.

Sensor 102 further includes a distal adapter 206 located at the distal end of the sensor 102 that is utilized to mechanically couple the distal end of the sensor 102 and a proximal end of the flexible distal end portion 110 (depicted in FIG. 3) in a way to further provide the above-described desired lateral bending direction to the membrane 201, as described below. Sensor 102 further includes an integrated circuit 201" adapted to at least one of convey signals and calculate pressure applied to the membrane 201.

In addition to the back housing portion 207 and the distal adaptor 206, sensor 102 includes a lead adapter 209 that is designed to further provide the above-described desired lateral bending direction to the membrane 201, as described below. In particular, sensor capsule 200 includes a feedthrough adaptor 208. A feedthrough pin 203 extends outward from the proximal end of the sensor 102 and through the feedthrough adaptor 208. During the connecting of the distal end 210 of the lead body to the sensor 102, a lead adaptor pin 205 located at the distal end 210 of the lead body 100 is electrically connected to the feedthrough pin 203 to enable electrical connection of the inner sensor bus coil 124 of the communication bus coil 127 via the sensor bus lumen 111 to the sensor capsule 200.

Figure 6A:
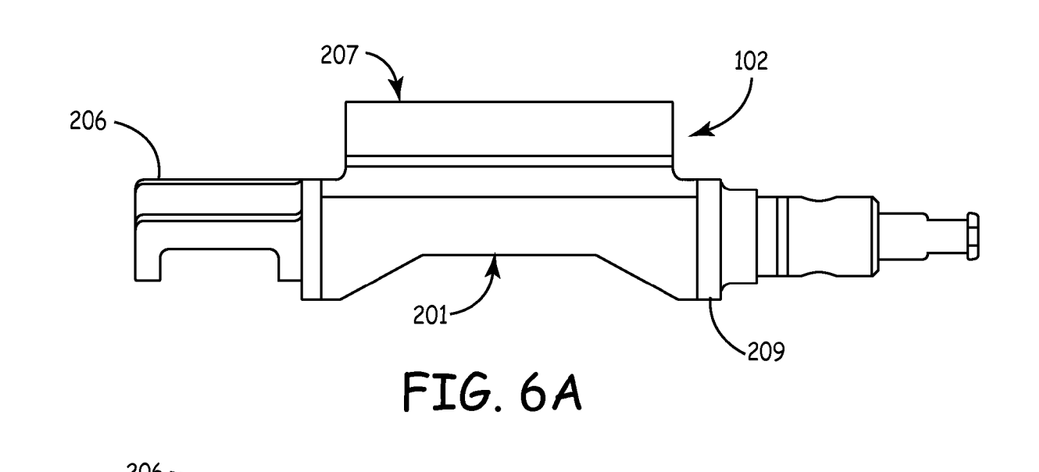
FIGS. 6A, 6B and 6C depict alternate view of the sensor depicted in FIGS. 5A and 5B; namely, an elevational side view, a plan view and a cross-sectional view.
Figure 6B:
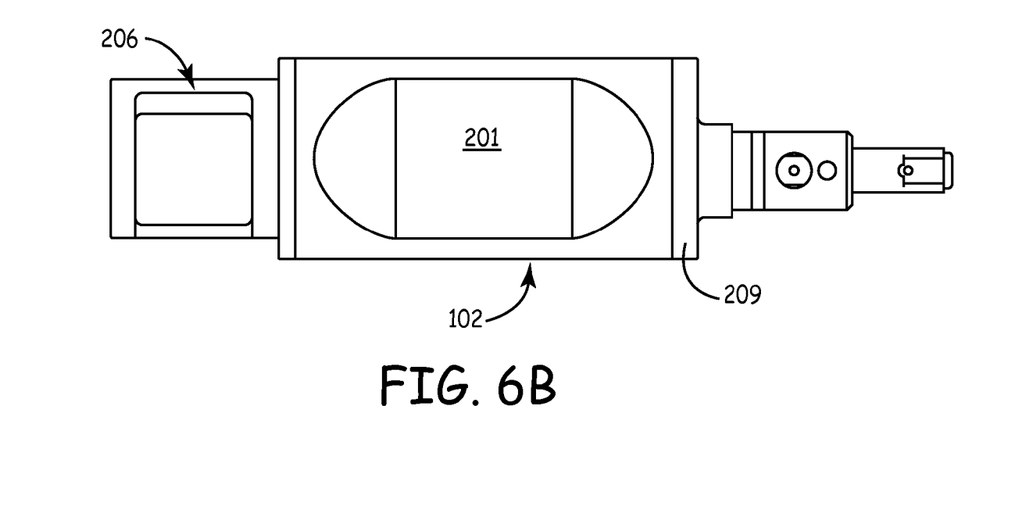
Figure 6C:
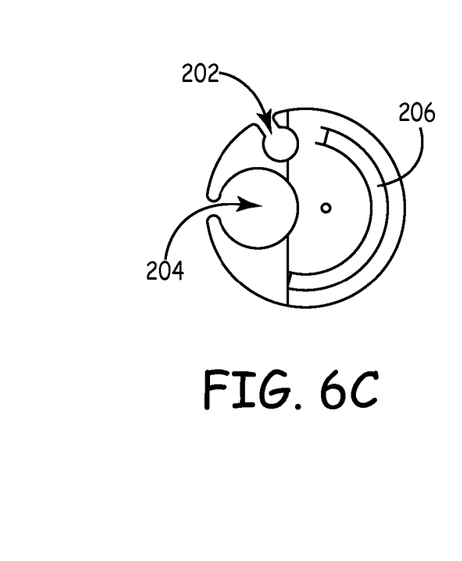

FIGS. 6A, 6B and 6C depict alternate views of the sensor package 200 depicted in FIGS. 5A and 5B; namely, an elevational side view, a plan view and a cross-sectional view. The bores 202, 204 of relatively thicker back portion 207 and the generally circular cross-sectional shape of the sensor 102 are depicted in FIG. 6C. The proximal and distal adapter 209, 206 are also depicted.

Figure 7:
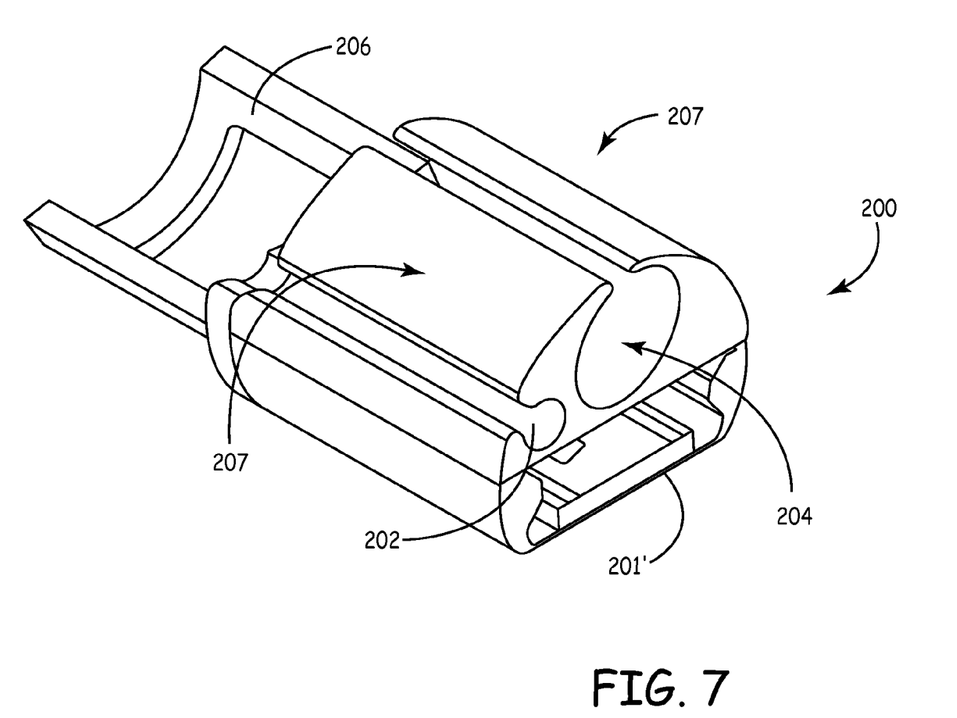
FIG. 7 is a perspective view illustrating the relatively thicker back portion of the sensor wherein the back portion includes two longitudinal bores for receiving an elongated conductor and a torque coil, respectively.
Figure 8:
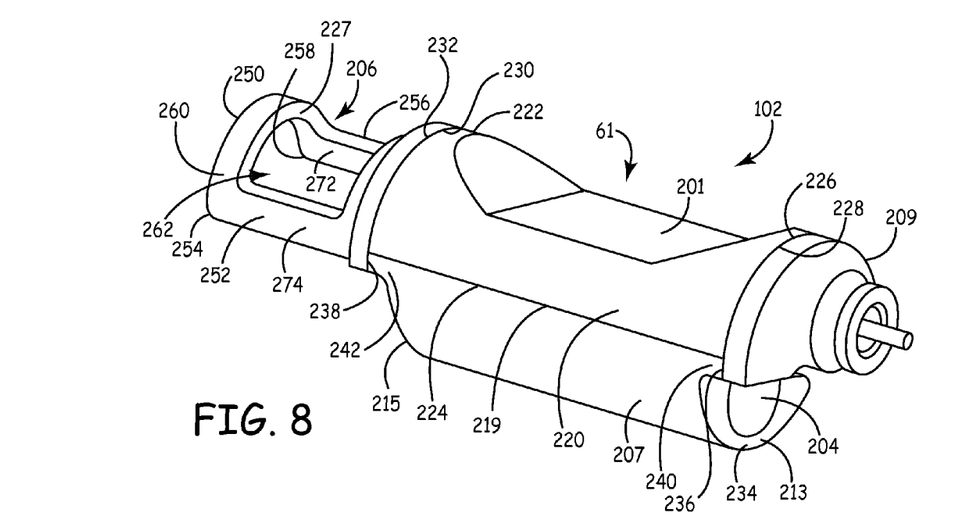
FIG. 8 is a perspective view of a sensor according to an embodiment of the disclosure.
Figure 8A:
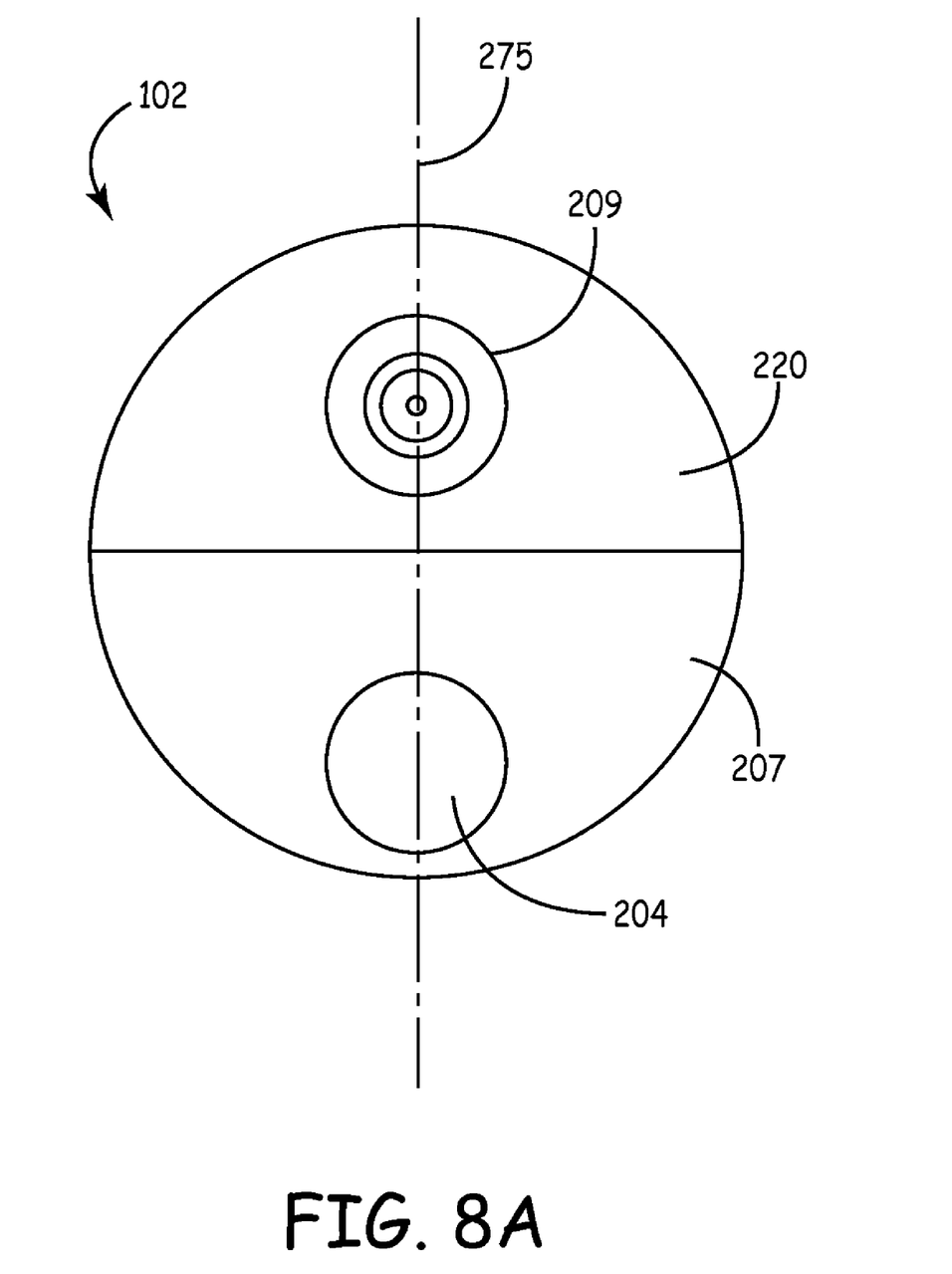
FIG. 8A is a plan view of a proximal end of the sensor of FIG. 8.

FIGS. 7 and 8 are perspective views of a sensor according to an embodiment of the disclosure. FIG. 8A is a plan view of a proximal end of the sensor of FIG. 8. In the embodiment of FIG. 7, the relatively thicker back housing portion 207 of the sensor package 200 includes two longitudinal bores 202, 204 for receiving an elongated conductor coupled to a distal ring electrode 113 and a torque coil 129, respectively (See FIGS. 1A-1C). The bores 202, 204 are depicted having an open longitudinal portion but such a portion is not required to practice the foregoing (see FIG. 8). In fact, the collar of the open portion of bores 202, 204 can extend radially outward from a position approximately from the maximum diameter of each respective bore. A portion of the pressure sensor integrated circuit 201" is also depicted in FIG. 7 disposed within the package 200.

In the embodiment of FIG. 8, the relatively thicker back housing portion 207 of the sensor package 200 includes only a single longitudinal bore 204 for receiving a torque coil 129 that extends to the tip electrode 16.

As illustrated in FIGS. 5, 7 and 8, a membrane portion 220 of sensor 102 includes the membrane 201 and sensor circuitry 201'. The membrane portion 220 extends from a top portion 222 to a bottom portion 224, the top portion 222 having the cutout portion 61 formed therein for exposing the membrane 201 to changes in pressure around the sensor 102. The membrane portion 220 extends from a proximal end 226 to a distal end 230. The proximal end 226 is located adjacent to a distal end 228 of the lead adaptor 209 and the distal end 230 is located proximal and adjacent to a proximal end 232 of the distal adaptor 206 of the sensor 102.

In addition, the bottom portion 219 of the back housing 207 includes a first flange 240 extending proximally relative to the proximal end 213 of the top portion 217 of the back housing 207, and a second flange 242 extending distally relative to the distal end 215 of the top portion 217 of the back housing 207. The first flange 240 extends proximally from the proximal end 213 of the back housing 207 to a first flange end 236 positioned distal and adjacent to the distal end 228 of the lead adaptor 209.

Similarly, the second flange 242 extends distally from the distal end 215 of the back housing 207 to a second flange end 238 positioned proximal and adjacent to the proximal end 232 of the distal adaptor 206 of the sensor 102. In this way, the top portion 217 of the back housing 207 extends a first length from the proximal end 217 to the distal end 215, while the bottom portion 219 extends a second length, greater than the first length, from the first flange end 236 to the second flange end 238. In addition, the second length associated with the bottom portion 219 of the back housing 207 is approximately equal to a length of the bottom 224 of the membrane portion 220 so that the bottom 224 of the membrane portion 220 is positioned to be aligned with and adjacent to the bottom 219 of the back housing 207, with the bore 204 for receiving the torque coil 129 being aligned with the lead adaptor 209 along a plane 107 (see FIG. 4) extending through a center axis 275 of both the bore 204 and the lead adaptor 209 (the plane 107 being substantially perpendicular to the above-described desired lateral direction) to promote the desired bending direction of the membrane 201, described above. Both the membrane portion 220 and the back housing 207 are semi-circular in shape to form the substantially circular shape of the sensor 102.

Figure 9:
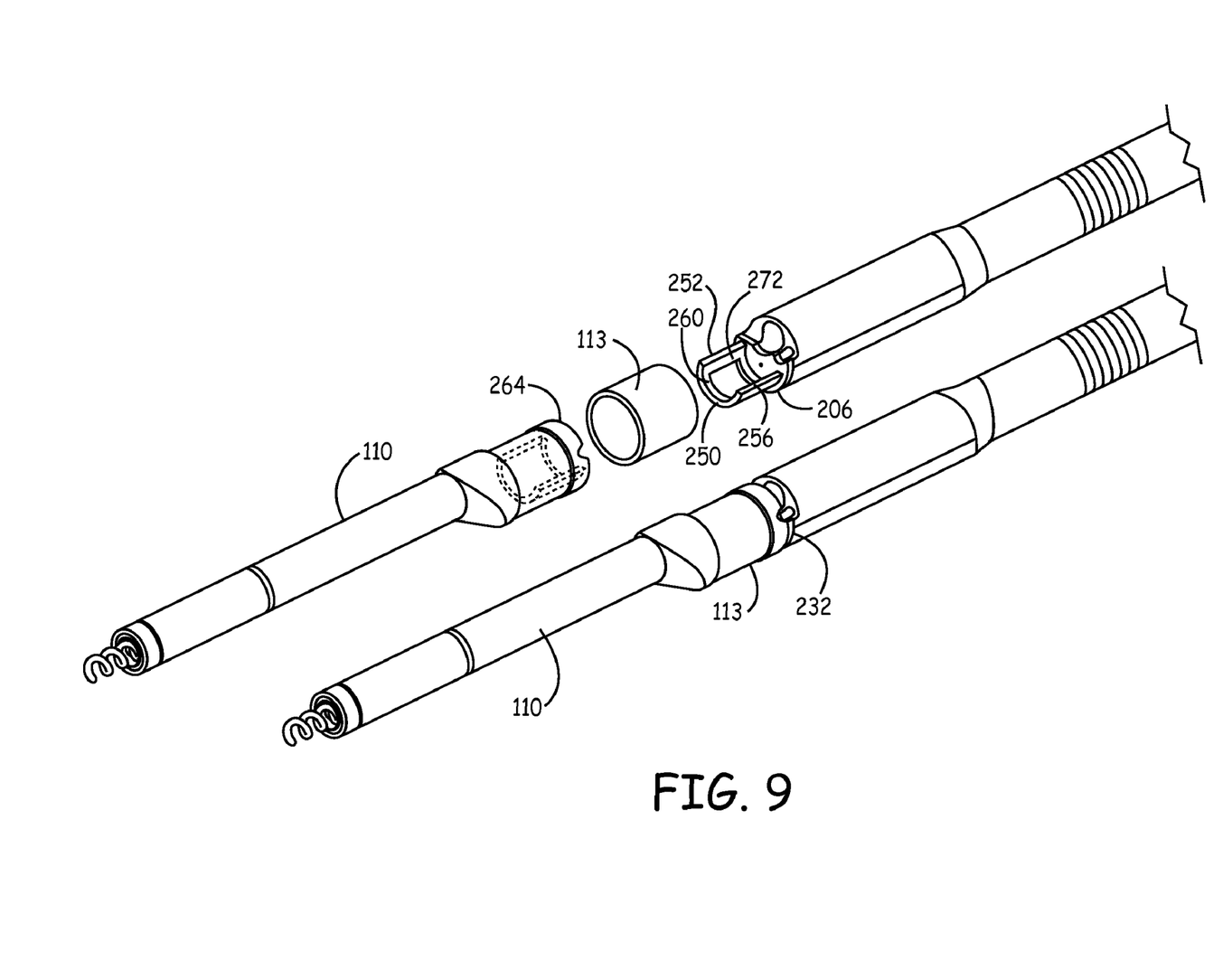
FIG. 9 is a perspective view of a distal end of a sensor lead according to an embodiment of the disclosure.

FIG. 9 is a perspective view of a distal end of a sensor lead according to an embodiment of the disclosure. As illustrated in FIGS. 8 and 9, distal adaptor 206 extends from the proximal end 232 to a distal end 250, the proximal end 232 being positioned adjacent to both the distal end 230 of membrane portion 220 and the second flange end 238 of the back housing 207. Distal adaptor 206 includes a first arm 252 that ends distally from the proximal end 238 of distal adaptor 206 to a first arm end 254, and a second arm 256 that extends distally from the proximal end 238 of distal adaptor 206 to a second arm end 258. A third arm 260 extends between the first arm end 254 and the second arm end 258 so that the first arm 252, the second arm 256, and the third arm 260 form an open portion 262. The third arm 260 has a semi-circular shape that conforms to the semi-circular shape of the distal end 230 of the membrane portion 220 of the sensor 102.

Figure 10:
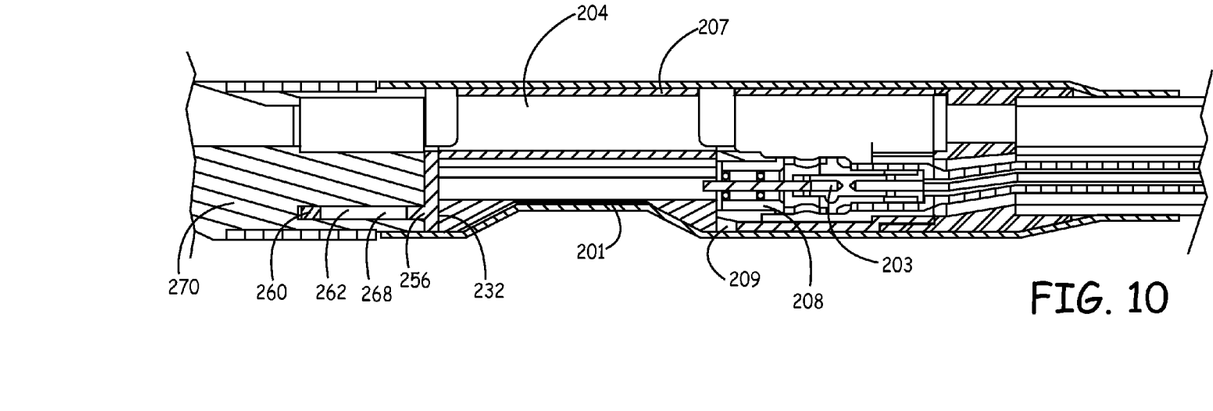
FIG. 10 is a cross-sectional view of a distal end of a sensor lead according to an embodiment of the disclosure.

FIG. 10 is a cross-sectional view of a distal end of a sensor lead according to an embodiment of the disclosure. As illustrated in FIGS. 8-10, a proximal end 264 of flexible member 110 is formed to receive the first arm 254, second arm 258 and third arm 260 of the distal adaptor 206 when the proximal end 264 of the flexible member 110 is positioned against the proximal end 232 of the distal adaptor 206. Once arms 254, 258 and 260 are positioned within the proximal end 264 of flexible member 110 and the proximal end 232 of the distal adaptor is engaged against the distal end 230 of the membrane portion 220 and the distal end 238 of the second flange 242 of the back housing 207, a medical adhesive 268 is injected and backfilled within open portion 262 and adheres to the silicone portion 270 of flexible member 110 positioned along the inner side 272 and the outer side 274 of the arms 254, 258 and 260. As a result, by positioning the adhesive 268 within open portion 262 to be secured against the silicone portion 270 both along the inner side 272 and the outer side 274 of the distal adaptor 206, an adhesive wedge is formed that engages against an inner wall 277 formed by the first arm 254, the second arm 258 and the third arm 260 that minimizes longitudinal movement of the distal adaptor 206, thus securing the distal adaptor 206 within the flexible member 110.

Figure 11:
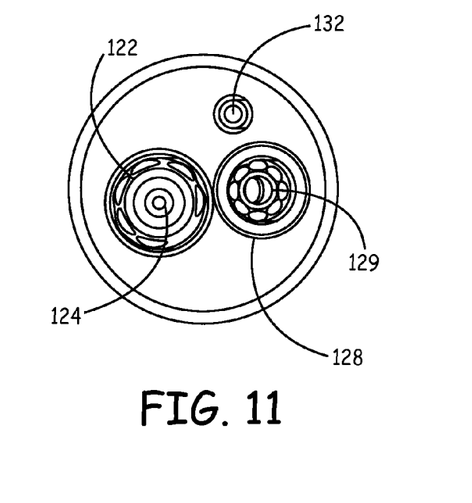
FIG. 11 is a cross-sectional elevational view of an embodiment of the lead body having just two coils and one separate cable.

FIG. 11 is a cross-sectional elevational view of an embodiment of the lead body having just two coils and one separate cable 132. One coil is the torque coil 129 which can be insulated with an polymer-based material 128 (especially where the coil 129 passes through the bore 204 of the titanium sensor package 200. The other coil is the sensor bus coil 122 having sensor bus cable 124 insulated from and located within the coil 122.

Figure 12:
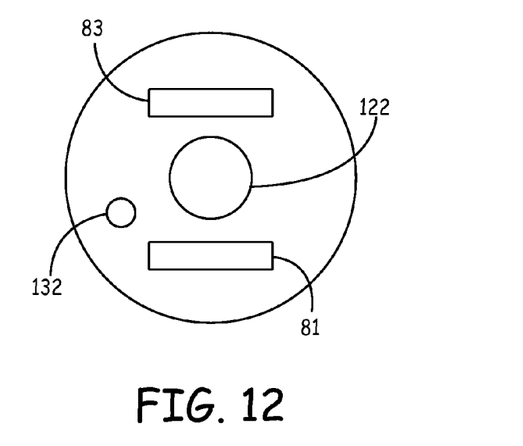
FIG. 12 is a cross-sectional elevational view of an embodiment of the lead body having just a single sensor bus coil and one separate cable.

FIG. 12 is a cross-sectional elevational view of an embodiment of the lead body having just a single sensor bus coil 122 and one separate cable 132. In addition, to increase "pushability" and to increase the likelihood that the lead body will bend in the desired direction, a pair of structure and/or lumens 81, 83 can be disposed alongside at least a portion of the coil 122. That is, one or both of the items 81, 83 tend to promote bending of the lead in the desired direction. The items 81, 83 can be coupled directly to sensor package 200 or can terminate proximal of the package 200. The items 81, 83 can comprise one or more elongated segments of resilient material, such a polymer or the like.

Figure 13:
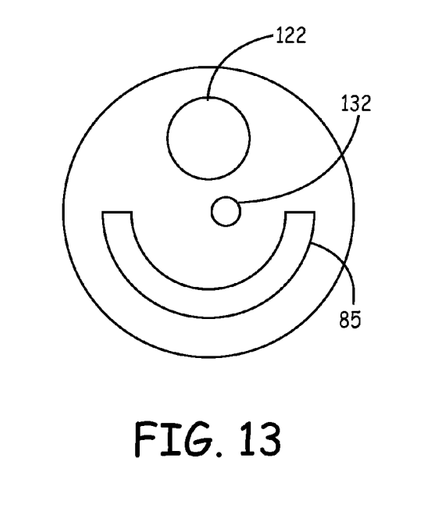
FIG. 13 is a cross-sectional elevational view of an embodiment of the lead body having just two coils and one separate cable.

FIG. 13 is a cross-sectional elevational view of an embodiment of the lead body having just two coils and one separate cable 132. In addition, to increase "pushability" and to increase the likelihood that the lead body will bend in the desired direction, a structure and/or lumen 85 can be disposed alongside at least a portion of the coil 122, such as a U-shaped structure or lumen depicted in FIG. 13. Of course, a variety of other shaped structures of lumen shapes can be utilized to achieve the advantages of the invention. That is, the item 85 tends to promote bending of the lead in the desired direction. The item 85 can be coupled directly to sensor package 200 or can terminate proximal of the package 200. The item 85 can comprise one or more elongated segments of resilient material, such a polymer or the like, or alternating segments of material and open lumen space.

Figure 14:
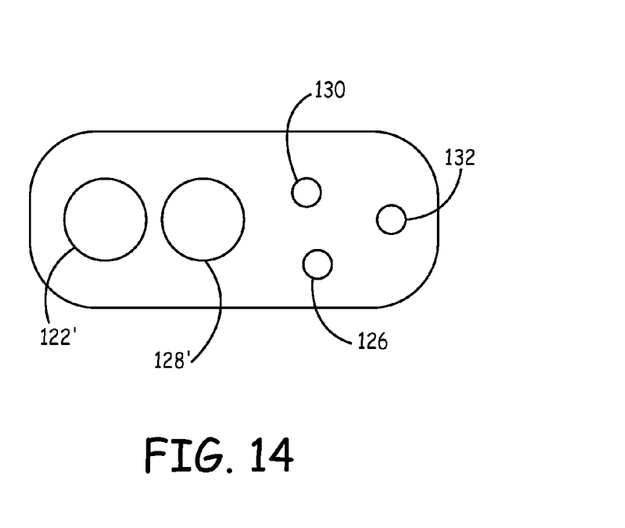
FIG. 14 is a cross-sectional elevational view of an embodiment of the lead body having a flattened cross-sectional appearance and two coils and three separate cables.

FIG. 14 is a cross-sectional elevational view of an embodiment of the lead body having a flattened cross-sectional appearance and two coils 122', 128' and three separate cables 126, 130, 132. As with prior embodiments, the coils tend to promote the lead to bend in the desired direction. In addition, the flattened cross-sectional shape of the lead body further encourages it to bend as desired thereby reducing signal artifacts and promoting operating stability of the pressure sensor and lead system.

It will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention. For example, the sensor could comprise an accelerometer (single- or multi-axis) which for any of a number of reasons might need to have reduced structure on one or more sides thereof thus becoming susceptible to the objects solved herein.

The invention claimed is:

1. A lead of an implantable medical device system, comprising:
   an elongated lead body;
   a sensor coupled to the lead body and extending from a proximal end to a distal end; and
   a distal lead adaptor having a first arm extending distally from the distal end of the sensor to a first arm end, a second arm extending distally from the distal end of the sensor to a second arm end, and a third arm extending between the first arm end and the second arm end, wherein the first arm, the second arm, and the third arm form an open portion.

2. The lead of claim 1, further comprising a flexible member having a proximal end formed to receive the first arm, the second arm, and the third arm when the proximal end of the flexible member is positioned against the proximal end of the sensor.

3. The lead of claim 2, further comprising a medical adhesive positioned within the open portion formed by the first arm, the second arm and the third arm, the medical adhesive adhering to a silicone portion of the flexible member and forming an adhesive wedge abutting the first arm, the second arm and the third arm to prevent longitudinal movement of the sensor from the flexible member.

4. The lead of claim 1, wherein the sensor comprises a pressure sensor for sensing changes in pressure along the sensor.

5. The lead of claim 1, wherein the sensor includes a membrane portion having a distal end positioned against a proximal end of the distal adaptor, wherein the third arm has a shape that conforms to a shape of the distal end of the membrane portion.

6. The lead of claim 5, further comprising:
   an electrode positioned distally from the sensor;
   a conductor coil extending through a lumen formed in the sensor, the lumen positioned below the membrane portion; and
   a lumen formed in the sensor for receiving the conductor coil as the conductor coil extends through the sensor, wherein the lumen and the lead adaptor are aligned along a center axis of both the lumen and the distal adaptor, the center axis being perpendicular to a longitudinal direction extending between the proximal end and the distal end of the sensor.

7. The lead of claim 6, further comprising a back housing positioned along the membrane portion and having a flange, wherein the lumen is formed in the back housing and the proximal end of the distal adaptor is engaged against both the distal end of the membrane portion and the flange.

8. An implantable medical device system, comprising:
   a device housing;
   a lead having an elongated lead body and a connector to electrically couple the lead to the housing;
   a sensor coupled to the lead body and extending from a proximal end to a distal end;
   a distal lead adaptor having a first arm extending distally from the distal end of the sensor to a first arm end, a second arm extending distally from the distal end of the sensor to a second arm end, and a third arm extending between the first arm end and the second arm end, wherein the first arm, the second arm, and the third arm form an open portion.

9. The implantable medical device system of claim 8, further comprising a flexible member having a proximal end formed to receive the first arm, the second arm, and the third arm when the proximal end of the flexible member is positioned against the proximal end of the sensor.

10. The implantable medical device system of claim 9, further comprising a medical adhesive positioned within the open portion formed by the first arm, the second arm and the third arm, the medical adhesive adhering to a silicone portion of the flexible member and forming an adhesive wedge abutting the first arm, the second arm and the third arm to prevent longitudinal movement of the sensor from the flexible member.

11. The implantable medical device system of claim 8, wherein the sensor comprises a pressure sensor for sensing changes in pressure along the sensor.

12. The implantable medical device system of claim 8, wherein the sensor includes a membrane portion having a distal end positioned against a proximal end of the distal adaptor, wherein the third arm has a shape that conforms to a shape of the distal end of the membrane portion.

13. The implantable medical device system of claim 12, further comprising:
   an electrode positioned distally from the sensor;
   a conductor coil extending through a lumen formed in the sensor, the lumen positioned below the membrane portion; and
   a lumen formed in the sensor for receiving the conductor coil as the conductor coil extends through the sensor, wherein the lumen and the lead adaptor are aligned along a center axis of both the lumen and the distal adaptor.

14. The implantable medical device system of claim 13, further comprising a back housing positioned along the membrane portion and having a flange, wherein the lumen is formed in the back housing and the proximal end of the distal adaptor is engaged against both the distal end of the membrane portion and the flange.

* * * * *